United States Patent
Tomita et al.

(10) Patent No.: US 9,752,971 B2
(45) Date of Patent: Sep. 5, 2017

(54) VISCOSITY MEASURING APPARATUS

(75) Inventors: Sho Tomita, Susono (JP); Rentaro Kuroki, Susono (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 238 days.

(21) Appl. No.: 14/408,026

(22) PCT Filed: Jun. 18, 2012

(86) PCT No.: PCT/JP2012/065542
§ 371 (c)(1),
(2), (4) Date: Dec. 15, 2014

(87) PCT Pub. No.: WO2013/190625
PCT Pub. Date: Dec. 27, 2013

(65) Prior Publication Data
US 2015/0101400 A1    Apr. 16, 2015

(51) Int. Cl.
| | | |
|---|---|---|
| *G01M 15/08* | (2006.01) | |
| *G01N 11/00* | (2006.01) | |
| *F01P 11/18* | (2006.01) | |
| *F02D 35/02* | (2006.01) | |
| *F01P 3/00* | (2006.01) | |

(52) U.S. Cl.
CPC ............. *G01N 11/00* (2013.01); *F01P 11/18* (2013.01); *G01M 15/08* (2013.01); *F01P 2003/001* (2013.01); *F02D 35/023* (2013.01); *F02D 2200/0614* (2013.01); *F02D 2200/1012* (2013.01); *G01N 2011/006* (2013.01); *G01N 2011/0093* (2013.01)

(58) Field of Classification Search
CPC  G01N 11/00; G01N 2011/0093; G01M 15/08
See application file for complete search history.

(56) References Cited

U.S. PATENT DOCUMENTS

2010/0057315 A1\* 3/2010 Yamamoto .......... F16H 57/0434
                                                            701/58
2012/0132154 A1    5/2012 Suzuki et al.

FOREIGN PATENT DOCUMENTS

| JP | H11-22461 A | 1/1999 |
|---|---|---|
| JP | 2004-169634 A | 6/2004 |
| JP | 2004285977 A \* | 10/2004 |

(Continued)

OTHER PUBLICATIONS

Kako et al. (JP 2004-169634 A), Jun. 2004, JPO Computer Translation.\*

*Primary Examiner* — Erika J Villaluna
(74) *Attorney, Agent, or Firm* — Andrews Kurth Kenyon LLP

(57) ABSTRACT

A viscosity measuring apparatus is mounted on a vehicle provided with an engine, a cylinder pressure sensor configured to detect cylinder pressure which is inner pressure of a cylinder of the engine, a fuel injection valve configured to supply fuel to the engine, and a temperature sensor configured to detect temperature of a coolant of the engine. The viscosity measuring apparatus is provided with: an estimating device configured to calculate a cooling loss from a heating value of the cylinder based on the cylinder pressure detected by the cylinder pressure sensor and an input heating value of the cylinder, and to estimate viscosity of the coolant on the basis of the calculated cooling loss.

3 Claims, 3 Drawing Sheets

(56) References Cited

FOREIGN PATENT DOCUMENTS

| JP | 2008-274909 A | 11/2008 |
|---|---|---|
| JP | 2010-181284 A | 8/2010 |
| JP | 4876202 B2 | 2/2012 |
| JP | 2012-072669 A | 4/2012 |
| WO | 03/027456 A1 | 4/2003 |
| WO | 2011/021511 A1 | 2/2011 |

* cited by examiner

VISCOSITY MEASURING APPARATUS

CROSS-REFERENCE TO RELATED APPLICATION

This is a national phase application based on the PCT International Patent Application No. PCT/JP2012/065542 filed Jun. 18, 2012, the entire contents of which are incorporated herein by reference.

TECHNICAL FIELD

The present invention relates to a viscosity measuring apparatus configured to measure viscosity of a liquid such as, for example, a coolant for cooling an engine which is mounted on a vehicle.

BACKGROUND ART

The liquid whose viscosity is measured by this type of apparatus is filled in a coolant circulation path of the engine, for example, as described in Patent literature 1. In the coolant circulation path, the coolant is boosted by a water pump, is supplied to a heat exchanger through a water jacket of the engine and a heater core, and is then returned to the water pump again.

CITATION LIST

Patent Literature

Patent Literature 1: Japanese Patent Application Laid Open No. 1111-022461

SUMMARY OF THE INVENTION

Technical Problem

By the way, the widely spread coolant is diluted ethylene glycol obtained by diluting ethylene glycol for preventing freezing with water to obtain necessary freezing temperature. Moreover, the coolant contains various additives to protect, for example, metal, rubber, resin or the like, which is used for the engine, a radiator or the like. The viscosity of the coolant is determined by, a ratio between ethylene glycol and water. The viscosity of ethylene glycol is higher than that of water.

Here, it is possible to reduce a cooling loss of the engine and to improve fuel efficiency by relatively increasing the concentration of ethylene glycol in the coolant to increase the concentration of the coolant. This, however, possibly causes overheating of the engine due to insufficient coolability caused by the relatively viscous coolant when the coolant is high-temperature (e.g. 100 degrees C.). Therefore, research and development have been carried out on a coolant having a relatively larger temperature change in viscosity than that of the conventional coolant (hereinafter referred to as a "viscosity variable LLC" as occasion demands").

For example, if the viscosity variable LLC is applied as the coolant of the engine, a control apparatus for the engine estimates the viscosity of the viscosity variable LLC, for example, from the temperature of the viscosity variable LLC, and controls the engine according to the estimated viscosity. In this case, a difference between an actual temperature change in viscosity of the viscosity variable LLC and a designed temperature change in viscosity possibly causes, for example, insufficient cooling of the engine, excessive cooling, or the like. This results in possible overheating and condensed water, which is technically problematic.

On the other hand, new provision of a viscometer or the like for measuring the viscosity of the viscosity variable LLC may cause technical problems such as, for example, an increase in the number of parts, a design change of piping or the like, and an increase in manufacturing cost.

It is therefore an object of the present invention to provide a viscosity measuring apparatus configured to indirectly measure the viscosity of the coolant.

Solution to Problem

The above object of the present invention can be achieved by a viscosity measuring apparatus mounted on a vehicle provided with an engine, a cylinder pressure sensor configured to detect cylinder pressure which is inner pressure of a cylinder of the engine, a fuel injection valve configured to supply fuel to the engine, and a temperature sensor configured to detect temperature of a coolant of the engine, said viscosity measuring apparatus is provided with: an estimating device configured to calculate a cooling loss from a heating value of the cylinder based on the cylinder pressure detected by the cylinder pressure sensor and an input heating value of the cylinder, and to estimate viscosity of the coolant on the basis of the calculated cooling loss.

According to the viscosity measuring apparatus of the present invention, the viscosity measuring apparatus is mounted on the vehicle provided with the engine, the cylinder pressure sensor, the fuel injection valve, and the temperature sensor. The cylinder pressure sensor detects the cylinder pressure for each cylinder of the engine. Various known aspects can be applied to the engine, the cylinder pressure sensor, the fuel injection valve and the temperature sensor, and thus, an explanation of the details thereof will be omitted.

The estimating device, which is provided, for example, with a memory, a processor or the like, calculates the cooling loss from the heating value of the cylinder based on the cylinder pressure detected by the cylinder pressure sensor and the input heating value of the cylinder, and estimates the viscosity of the coolant on the basis of the calculated cooling loss.

Various known aspects can be applied to a method of obtaining the heating value of the cylinder from the cylinder pressure detected by the cylinder pressure sensor, and thus, an explanation of the details thereof will be omitted. The input heating value of the cylinder may be obtained, for example, on the basis of number of revolutions of the engine, a flow rate of the fuel, the heating value of the fuel, or the like. Various known aspects can be also applied to a method of obtaining the input heating value.

The cooling loss is obtained by subtracting the heating value of the cylinder from the input heating value of the cylinder. Here, a difference between the input heating value of the cylinder and the heating value of the cylinder is, strictly speaking, the sum of the cooling loss and an unburned fuel loss; however, it has been found by the study of the present inventors that the unburned fuel low is negligibly smaller than the cooling loss in some operating condition. Therefore, as described above, a value obtained by subtracting the heating value of the cylinder from the input heating value of the cylinder can be considered to be the cooling loss.

If a relation between the cooling loss and the viscosity of the coolant is studied in advance, for example, at a design step and is stored in a memory as a map or the like, it is then possible to estimate the viscosity of the coolant from the stored map on the basis of the calculated cooling loss.

As a result, according to the viscosity measuring apparatus of the present invention, it is possible to indirectly measure the viscosity of the coolant on the basis of the cooling loss.

In one aspect of the viscosity measuring apparatus of the present invention, the viscosity measuring apparatus is further provided with a determining device configured to determine that the viscosity is abnormal if the estimated viscosity deviates from a designed value of the coolant by a predetermined value or more.

According to this aspect, it is possible to prevent the overheating or the like, for example, by informing a driver of the abnormal coolant or by performing similar actions according to a determination result of the determining device, which is extremely useful in practice.

The "predetermined value" may be set, for example, on the basis of a relation between the viscosity of the coolant and the temperature of the engine which is obtained by experiments or simulations. Specifically, for example, the viscosity of the coolant with insufficient cooling may be set as a viscous-side predetermined value, and the viscosity of the coolant with excessive cooling may be set as a less-viscous-side predetermined value In this aspect, the estimation of the viscosity by said estimating device and the determination of the abnormal viscosity by said determining device can be performed if each of a time differential value of number of revolutions of the engine, a time differential value of an injection quantity of the fuel injection valve, and a time differential value of the temperature detected by the temperature sensor is less than or equal to respective one of predetermined values.

By virtue of such a configuration, it is possible to prevent a reduction in estimation accuracy of the viscosity, and to prevent the determination of the abnormal viscosity based on the viscosity obtained with relatively low estimation accuracy.

The operation and other advantages of the present invention will become more apparent from an embodiment explained below.

DESCRIPTION OF EMBODIMENTS

An embodiment of the viscosity measuring apparatus of the present invention will be explained with reference to the drawings.

Figure 1:
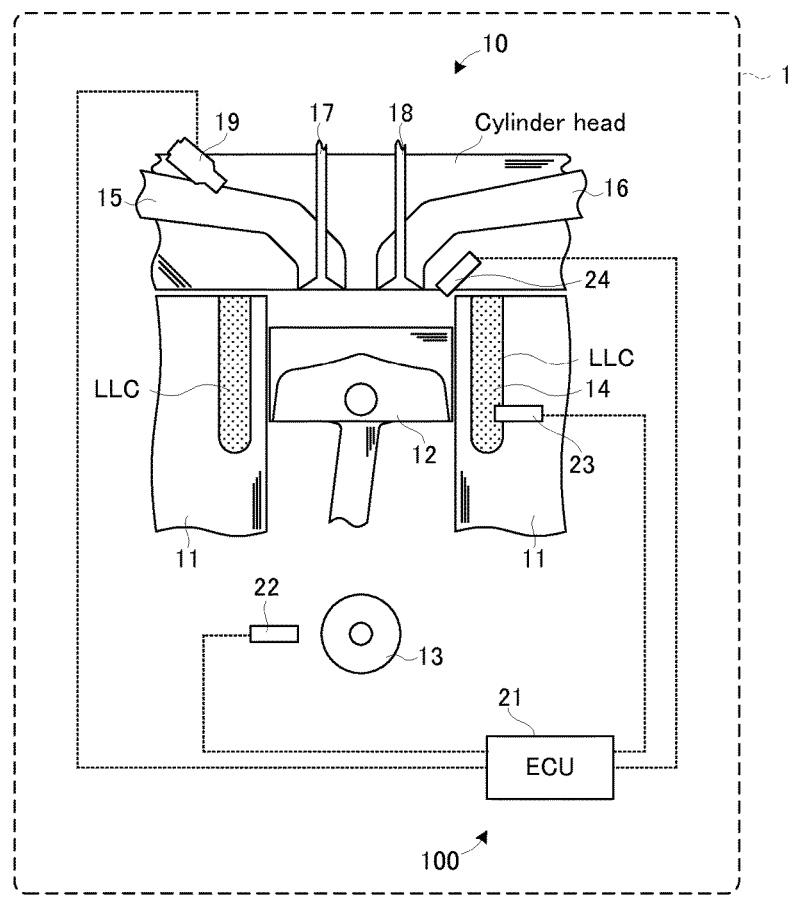
FIG. 1 is a block diagram illustrating a configuration of a vehicle in an embodiment.

Firstly, a configuration of a vehicle in the embodiment will be explained with reference to FIG. 1. FIG. 1 is a block diagram illustrating the configuration of the vehicle in the embodiment.

In FIG. 1, a vehicle 1 is provided with an engine 10 and an electronic control unit (ECU) 21 for various electronic control of the vehicle 1.

The engine 10 is provided with cylinder bores 11, a piston 12, a crankshaft 13, a water jacket, an intake passage 15, an exhaust passage 16, an intake valve 17, an exhaust valve 18, and a fuel injection valve 19. The engine 10 is also provided with a crank angle sensor 22, a temperature sensor 23, and a cylinder pressure sensor 24.

Figure 2:
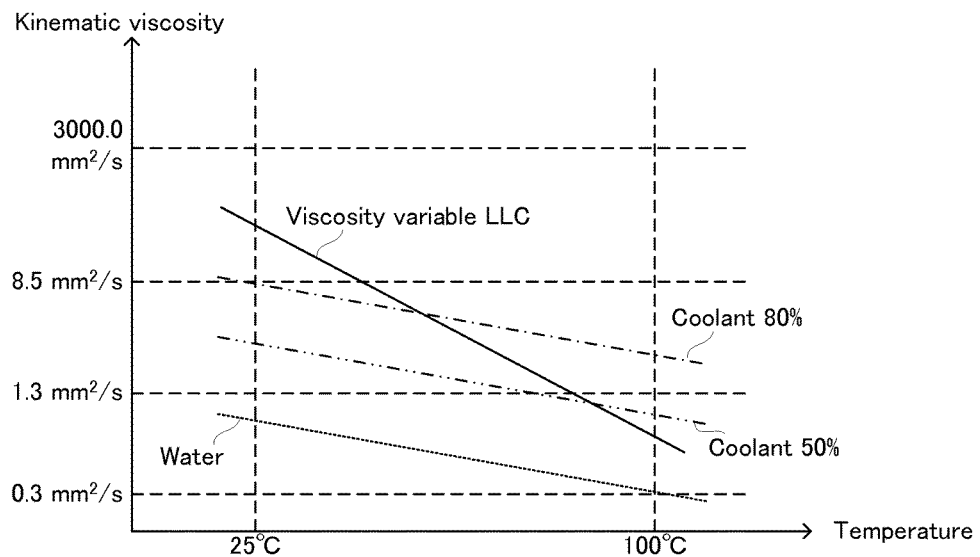
FIG. 2 is a conceptual diagram illustrating one example of characteristics of a viscosity variable LLC.

The engine 10 in the embodiment is an engine optimized for a viscosity variable LLC. Now, the viscosity variable LLC will be explained with reference to FIG. 2. FIG. 2 is a conceptual diagram illustrating one example of characteristics of the viscosity variable LLC. In FIG. 2, a vertical axis is log (log Y) and a horizontal axis is log X.

As illustrated in FIG. 2, for example, the viscosity variable LLC has a kinematic viscosity of 8.5 $mm^2/s$ to 3000.0 $mm^2/s$ at 25 degrees C. and has a kinematic viscosity of 0.3 $mm^2/s$ to 1.3 $mm^2/s$ at 100 degrees C. As illustrated in FIG. 2, it is clear that a temperature change in viscosity of the viscosity variable LLC is much greater than a temperature change in viscosity of a general coolant (refer to "coolant 50%" in FIG. 2) or water.

An ECU 21 in the embodiment controls the engine 10 under the assumption that a predetermined viscosity variable LLC 14 is filled in the engine 10. Therefore, a difference between the temperature change in viscosity of the LLC and a designed temperature change in viscosity of the LLC, for example, due to the filling of a conventional LLC or for similar reasons, possibly has an adverse effect on the engine 10.

Specifically, for example, the viscosity of the LLC that is too high compared to the designed value causes insufficient cooling, clogging with the LLC or the like. On the other hand, the viscosity of the LLC that is too low compared to the designed value causes excessive cooling. This results in possible overheating and condensed water.

Therefore, in the embodiment, the viscosity of the LLC 14 is measured by a viscosity measuring apparatus 100. The viscosity measuring apparatus 100 is provided with the ECU 21 configured to estimate the viscosity of the LLC 14 and determine that the viscosity is abnormal if the estimated viscosity of the LLC 14 deviates from the designed value by a predetermined value or more.

The "ECU 21" in the embodiment is one example of the "estimating device" and the "determining device" of the present invention. In other words, a part of the function of the ECU 21 for various electronic control of the vehicle 1 is used as a part of the viscosity measuring apparatus 100.

Figure 3:
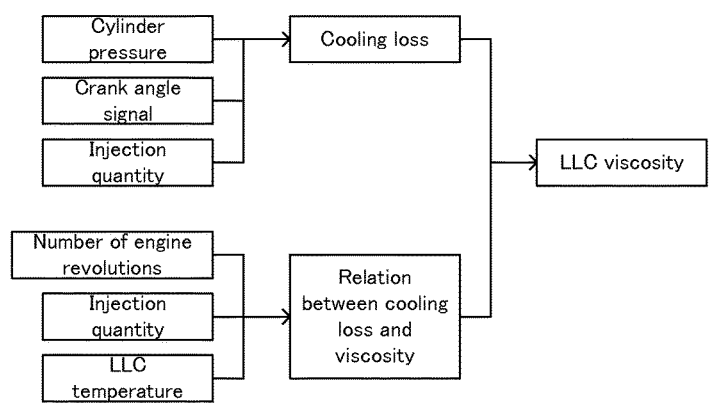
FIG. 3 is a diagram illustrating a coolant viscosity estimation flow in the embodiment.

The ECU 21 as a part of the viscosity measuring apparatus 100 calculates a heating value or calorific value of the cylinder on the basis of cylinder pressure measured by the cylinder pressure sensor 24. The ECU 21 also calculates an input heating value of the cylinder on the basis of an output signal of the crank angle sensor 22, an injection quantity of the fuel injection valve 19, or the like. The ECU 21 then calculates, as a cooling loss, a value obtained by subtracting the calculated heating value from the calculated input heating value (refer to FIG. 3).

Figure 4:
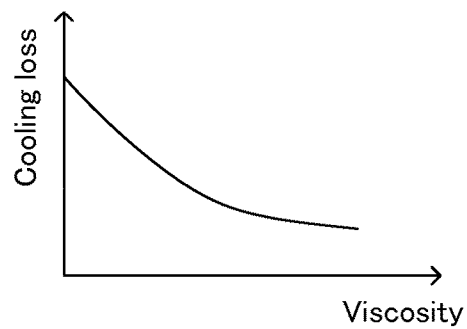
FIG. 4 is a diagram illustrating one example of a map for specifying a relation between the viscosity of the LLC and a cooling loss.

In parallel with the calculation of the cooling loss, the ECU 21 determines a map (refer to FIG. 4) for specifying a relation between the viscosity of the LLC 14 and the cooling loss, which corresponds to an operating condition of the engine 10 and the temperature of the LLC 14, wherein the operating condition of the engine 10 is determined according to the injection quantity of the fuel injection valve 19 and the number of revolutions of the engine 10 based on the output signal of the crank angle sensor 22, and the temperature of the LLC 14 is measured, by the temperature sensor 23. The ECU 21 then estimates the viscosity of the LLC 14 from the calculated cooling loss and the map as illustrated in FIG. 4.

Figure 5:
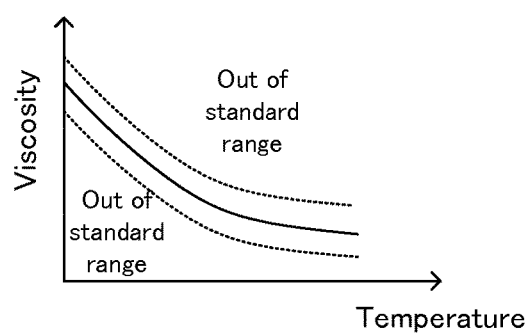
FIG. 5 is a diagram illustrating one example of a map for defining an allowable range of the viscosity of the LLC.

The ECU 21 then determines whether or not a relation between the estimated viscosity of the LLC 14 and the temperature of the LLC 14 measured by the temperature sensor 23 corresponds to being out of a standard range, for example, as illustrated in FIG. 5. If it is determined that it correspond to being out of the standard range (i.e. the viscosity is abnormal), the ECU 21 informs a driver of the vehicle 1 of the abnormal viscosity of the LLC 14, for example, by lighting a MIL (not illustrated) or the like.

Here, in particular, the ECU 21 estimates the viscosity of the LLC 14 in the condition that each of a time differential value of the number of revolutions of the engine 10, a time differential value of the injection quantity of the fuel injection valve 19, and a time differential value of the temperature detected by the temperature sensor 23 is less than or equal to respective one of predetermined values, and also performs the determination of the abnormal viscosity.

By virtue of such a configuration, it is possible to prevent a reduction in estimation accuracy of the viscosity of the LLC 14 caused, for example, by an unstable flow rate of the LLC.

The present invention is not limited to the aforementioned embodiments, but various changes may be made, if desired, without departing from the essence or spirit of the invention which can be read from the claims and the entire specification. A viscosity measuring apparatus, which involves such changes, is also intended to be within the technical scope of the present invention.

DESCRIPTION OF REFERENCE NUMERALS AND LETTERS

1 hybrid vehicle
10 engine
11 cylinder bore
12 piston
13 crankshaft
14 LLC
15 intake passage
16 exhaust passage
17 intake valve
18 exhaust valve
19 fuel injection valve
21 ECU
22 crank angle sensor
23 temperature sensor
24 cylinder pressure sensor
100 viscosity measuring apparatus

The invention claimed is:

1. A viscosity measuring apparatus mounted on a vehicle comprising an engine, a cylinder pressure sensor configured to detect cylinder pressure which is inner pressure of a cylinder of the engine, a fuel injection valve configured to supply fuel to the engine, and a temperature sensor configured to detect temperature of a coolant of the engine, said viscosity measuring apparatus comprising:
an estimating device configured to calculate a cooling loss from a heating value of the cylinder based on the cylinder pressure detected by the cylinder pressure sensor and an input heating value of the cylinder, and to estimate viscosity of the coolant on the basis of a relation between the viscosity of the coolant and a cooling loss, which is led from an operation condition of the engine and the temperature of the coolant detected by said temperature sensor, and the calculated cooling loss.

2. The viscosity measuring apparatus according to claim 1, further comprising a determining device configured to determine that the viscosity is abnormal if the estimated viscosity deviates from a designed value of the coolant by a predetermined value or more.

3. The viscosity measuring apparatus according to claim 2, wherein the estimation of the viscosity by said estimating device and the determination of the abnormal viscosity by said determining device are performed if each of a time differential value of number of revolutions of the engine, a time differential value of an injection quantity of the fuel injection valve, and a time differential value of the temperature detected by the temperature sensor is less than or equal to respective one of predetermined values.

* * * * *

UNITED STATES PATENT AND TRADEMARK OFFICE
CERTIFICATE OF CORRECTION

| | | |
|---|---|---|
| PATENT NO. | : 9,752,971 B2 | Page 1 of 1 |
| APPLICATION NO. | : 14/408026 | |
| DATED | : September 5, 2017 | |
| INVENTOR(S) | : Sho Tomita et al. | |

It is certified that error appears in the above-identified patent and that said Letters Patent is hereby corrected as shown below:

In the Specification

At Column 1, Line 33 change the content from "No. 1111-022461" to "No. H11-022461"

Signed and Sealed this
Twenty-ninth Day of May, 2018

Andrei Iancu
*Director of the United States Patent and Trademark Office*